(12) United States Patent
Chambers et al.

(10) Patent No.: US 10,704,210 B2
(45) Date of Patent: Jul. 7, 2020

(54) SYSTEM AND METHOD FOR ASPHALT MIX TRACKING

(71) Applicant: Astec, Inc., Chattanooga, TN (US)

(72) Inventors: Mark Chambers, Rossville, GA (US); Harold Crowe, Dayton, TN (US); Kris Robertson, Chickamauga, GA (US); Albert Covington, Cleveland, TN (US); Wayne Hall, Chattanooga, TN (US); Jonathan Brown, Ringgold, GA (US); Chuck Simpson, Soddy Daisy, TN (US); Lien Gangte, Burnaby (CA)

(73) Assignee: Astec, Inc., Chattanooga, TN (US)

( * ) Notice: Subject to any disclaimer, the term of this patent is extended or adjusted under 35 U.S.C. 154(b) by 396 days.

(21) Appl. No.: 15/597,834

(22) Filed: May 17, 2017

(65) Prior Publication Data

US 2017/0335525 A1 Nov. 23, 2017

Related U.S. Application Data

(60) Provisional application No. 62/337,485, filed on May 17, 2016.

(51) Int. Cl.
*E01C 23/01* (2006.01)
*E01C 19/18* (2006.01)
(Continued)

(52) U.S. Cl.
CPC .............. *E01C 23/01* (2013.01); *E01C 11/00* (2013.01); *E01C 19/18* (2013.01); *G01N 33/42* (2013.01); *G06K 7/10009* (2013.01); *G06Q 10/08* (2013.01); *G06Q 10/0833* (2013.01); *G06Q 50/08* (2013.01); *E01C 19/10* (2013.01)

(58) Field of Classification Search
CPC .......... E01C 23/01; E01C 11/00; E01C 19/18; E01C 19/10; G01N 33/42; G06K 7/10009; G06Q 10/08; G06Q 10/0833; G06Q 50/08
See application file for complete search history.

(56) References Cited

U.S. PATENT DOCUMENTS 7,455,217 B2 * 11/2008 Taylor ................ G06K 7/10336
235/375
2008/0252483 A1 * 10/2008 Hodges .................... G08G 1/02
340/905

(Continued)

*Primary Examiner* — A. Hunter Wilder
*Assistant Examiner* — Joseph M Mutschler
(74) *Attorney, Agent, or Firm* — Chambliss, Bahner & Stophel, P.C.

(57) ABSTRACT

An asphalt mix tracking system having a data collection system adapted to determine at least one characteristic of the asphalt mix, a data control system adapted to receive data from the data collection system, a lot tracking system adapted to track a lot of the asphalt mix, a truck tracking system adapted to track a truck, and a pavement injection system adapted to identify the lot of the asphalt mix. The preferred asphalt mix tracking system is adapted to substantially continuously track the asphalt mix from a mixing site to a paving site. A method for tracking an asphalt mix including determining the at least one characteristic of the asphalt mix, communicating the at least one characteristic of the asphalt mix to the data control system, transporting the asphalt mix from the mixing site to the paving site, and injecting an identification means at the paving site.

16 Claims, 5 Drawing Sheets

(51) Int. Cl.
*E01C 11/00* (2006.01)
*G01N 33/42* (2006.01)
*G06K 7/10* (2006.01)
*G06Q 10/08* (2012.01)
*G06Q 50/08* (2012.01)
*E01C 19/10* (2006.01)

(56) References Cited

U.S. PATENT DOCUMENTS

| | | | | |
|---|---|---|---|---|
| 2013/0136539 A1* | 5/2013 | Aardema | ............... | G01K 1/024 |
| | | | | 404/75 |
| 2013/0290062 A1* | 10/2013 | Patel | ................ | G06Q 10/06313 |
| | | | | 705/7.23 |
| 2017/0058467 A1* | 3/2017 | Marsolek | ............ | E01C 19/1063 |

* cited by examiner

SYSTEM AND METHOD FOR ASPHALT MIX TRACKING

CROSS-REFERENCES TO RELATED APPLICATIONS/PATENTS

This application relates back to and claims the benefit of priority from U.S. Provisional Application for Patent Ser. No. 62/337,485 titled "Mix Tracking System" and filed on May 17, 2016.

FIELD OF THE INVENTION

The present invention relates generally to systems and methods for tracking products, and particularly to systems and methods for tracking asphalt mix.

BACKGROUND AND DESCRIPTION OF THE PRIOR ART

It is known to use systems and methods to track asphalt mix. Conventional systems and methods, however, suffer from one or more disadvantages. For example, conventional asphalt mix tracking systems and methods do not track the asphalt mix from the mixing site all the way to the paving site. Conventional asphalt mix tracking systems and methods also do not install identification means in the paved roadway at intervals. Conventional asphalt mix tracking systems and methods do not sufficiently provide the age of the paved roadway or the origin or composition of its asphalt mix at a later date. In addition, conventional asphalt mix tracking systems and methods do not permit such data to be collected via a vehicle while its travels on the paved roadway. Conventional asphalt mix tracking systems and methods also do not efficiently share data with multiple parties. Further, conventional asphalt mix tracking systems and methods do not sufficiently facilitate the reclamation and recycling of asphalt pavement. Still further, conventional asphalt mix tracking systems and methods do not sufficiently minimize the incidence of "out of tolerance" asphalt mixes. Additionally, conventional asphalt mix tracking systems do not sufficiently reduce waste and costs.

It would be desirable, therefore, if a system and method for asphalt mix tracking could be provided that would track the asphalt mix from the mixing site all the way to the paving site. It would also be desirable if such system and method for asphalt mix tracking could be provided that would, install identification means in the paved roadway at intervals. It would be further desirable if such a system and method for asphalt mix tracking could be provided that would provide the age of the paved roadway or the origin or composition of its asphalt mix at a later date. It would be still further desirable if such a system and method for asphalt mix tracking could be provided that would permit such data to be collected via a vehicle while its travels on the paved roadway. It would also be desirable if such system and method for asphalt mix tracking could be provided that would permit such data to be collected via a vehicle while its travels on the paved roadway. It would be further desirable if such a system and method for asphalt mix tracking could be provided that would efficiently share data with multiple parties. It would be still further desirable if such a system and method for asphalt mix tracking could be provided that would facilitate the reclamation and recycling of asphalt pavement. It would also be desirable if such system and method for asphalt mix tracking could be provided that would reduce waste and costs.

Advantages of the Preferred Embodiments of the Invention

Accordingly, it is an advantage of the preferred embodiments of the invention claimed herein to provide a system and method for asphalt mix tracking that tracks the asphalt mix from the mixing site all the way to the paving site. It is also an advantage of the preferred embodiments of the invention claimed herein to provide a system and method for asphalt mix tracking that installs an identification means in the paved roadway at intervals. It is another advantage of the preferred embodiments of the invention claimed herein to provide a system and method for asphalt mix tracking that provides the age of the paved roadway or the origin or composition of its asphalt mix at a later date. It is still another advantage of the preferred embodiments of the invention claimed herein to provide a system and method for asphalt mix tracking that permits such data to be collected via a vehicle while its travels on the paved roadway. It is yet another advantage of the preferred embodiments of the invention claimed herein to provide a system and method for asphalt mix tracking that efficiently shares data with multiple parties. It is a further advantage of the preferred embodiments of the invention claimed herein to provide a system and method for asphalt mix tracking that facilitates the reclamation and recycling of asphalt pavement. It is a still further advantage of the preferred embodiments of the invention claimed herein to provide a system and method for asphalt mix tracking that reduces waste and costs.

Additional advantages of the preferred embodiments of the invention will become apparent from an examination of the drawings and the ensuing description.

Explanation of the Technical Terms

As used herein, the term "measuring device" means any device, mechanism, assembly, or combination thereof that is adapted to determine one or more characteristics of an object or material such as an asphalt mix. The term "measuring device" includes without limitation aggregate weighbridges, recycle weighbridges, temperature sensors, bin scales, bin on-load cells, truck scales, hopper scales, batching scales, metering pumps, bin level indicators, tank level indicators, Coriolis meters, load cells, pressure sensors, moisture probes, drive speed encoders, belt speed encoders, no-rotation sensors, bin weighbridges, and the like.

As used herein, the term "controller" means any device, mechanism, assembly, or combination thereof that is adapted to control an application or process using computer logic. The term "controller" includes without limitation programmable logic controllers, microcontrollers, and microprocessors.

As used herein, the term "server" means any program, process, device, mechanism, assembly, or combination thereof that is adapted to electronically communicate with a controller as defined above and be electronically accessed by remote devices. The term "server" includes without limitation programs, processes, devices, mechanisms, assemblies, and combinations thereof that are electronically connected to a network of controllers and are adapted to provide a service in response to a request from one or more controllers. The term "server" further includes without limitation programs, processes, devices, mechanisms, assemblies, and combinations thereof that are adapted to provide a service to one or more controllers on a publish-subscribe basis. The term "server" still further includes without limitation application servers, catalog servers, communications servers, computing servers, database servers, the Internet, the "cloud," and the like.

As used herein, the term "tag" means any device, mechanism, assembly, or combination thereof that is adapted to be attached to or placed in the object or material being measured by the measuring device. The term "tag" includes without limitation devices, mechanisms, assemblies, and combinations thereof that are adapted to wirelessly communicate with a reader as defined below. The term "tag" further includes without limitation active, passive, battery-operated passive, and field-programmable tags.

As used herein, the term "reader" means any device, mechanism, assembly, or combination thereof that is adapted to wirelessly communicate with a tag as defined above and a controller as defined above. The term "reader" includes without limitation passive and active readers. The term "reader" further includes without limitation fixed and mobile readers.

Notes on Construction

The use of the terms "a", "an", "the" and similar terms in the context of describing the invention are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. The terms "substantially", "generally" and other words of degree are relative modifiers intended to indicate permissible variation from the characteristic so modified. The use of such terms in describing a physical or functional characteristic of the invention is not intended to limit such characteristic to the absolute value which the term modifies, but rather to provide an approximation of the value of such physical or functional characteristic. All methods described herein can be performed in any suitable order unless otherwise specified herein or clearly indicated by context.

The use of any and all examples or exemplary language (e.g., "such as" and "preferably") herein is intended merely to better illuminate the invention and the preferred embodiments thereof, and not to place a limitation on the scope of the invention. Nothing in the specification should be construed as indicating any element as essential to the practice of the invention unless so stated with specificity.

SUMMARY OF THE INVENTION

The apparatus of the invention comprises an asphalt mix tracking system having a data collection system that is adapted to determine at least one characteristic of the asphalt mix, a data control system that is adapted to receive data from the data collection system, a lot tracking system that is adapted to track a lot of the asphalt mix, a truck tracking system that is adapted to track a truck, and a pavement injection system that is adapted to identify the lot of the asphalt mix. The preferred asphalt mix tracking system is adapted to substantially continuously track the asphalt mix from a mixing site to a paving site.

The method of the invention comprises a method for tracking an asphalt mix comprises providing an asphalt mix tracking system. The preferred asphalt mix tracking system comprises a data collection system that is adapted to determine at least one characteristic of the asphalt mix, a data control system that is adapted to receive data from the data collection system, a lot tracking system that is adapted to track a lot of the asphalt mix, a truck tracking system that is adapted to track a truck, and a pavement injection system that is adapted to identify the lot of the asphalt mix. The preferred asphalt mix tracking system is adapted to substantially continuously track the asphalt mix from a mixing site to a paving site. The preferred method for tracking an asphalt mix also comprises determining the at least one characteristic of the asphalt mix, communicating the at least one characteristic of the asphalt mix to the data control system, transporting the asphalt mix from the mixing site to the paving site, and injecting an identification means at the paving site.

BRIEF DESCRIPTION OF THE DRAWINGS

The presently preferred embodiments of the invention are illustrated in the accompanying drawings, in which like reference numerals represent like parts throughout, and in which.

DESCRIPTION OF THE PREFERRED EMBODIMENTS OF THE INVENTION

Figure 1:
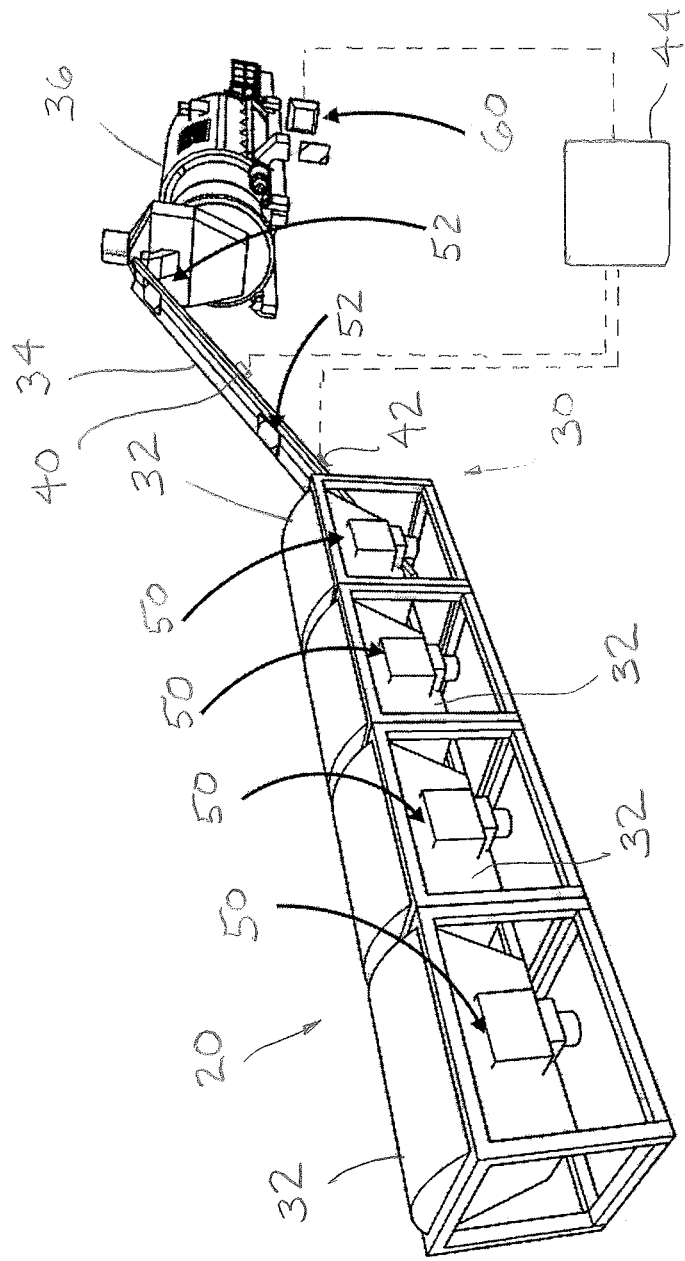
FIG. 1 is a perspective view of an exemplary mixing site utilizing the preferred embodiment of the asphalt tracking system in accordance with the present invention.

Referring now to the drawings, the preferred embodiment of the system and method for asphalt mix tracking in accordance with the present invention is illustrated by FIGS. 1 through 5. As shown in FIGS. 1-5, the preferred system and method for asphalt mix tracking is adapted to substantially continuously track the asphalt mix from the mixing site all the way to the paving site. The preferred system and method for asphalt mix tracking also installs an identification means in a paved roadway at intervals. The preferred system and method for asphalt mix tracking further provides the age of the paved roadway or the origin or composition of its asphalt mix at a later date. The preferred system and method for asphalt mix tracking still further permits such data to be collected via a vehicle while its travels on the paved roadway. The preferred system and method for asphalt mix tracking also efficiently shares data with multiple parties via remote devices. In addition, the preferred system and method for asphalt mix tracking facilitates the reclamation and recycling of asphalt pavement. The preferred system and method for asphalt mix tracking further reduces waste and costs.

Referring now to FIG. 1, a perspective view of an exemplary mixing site utilizing the preferred embodiment of the asphalt tracking system in accordance with the present invention is illustrated. As shown in FIG. 1, the exemplary mixing site is designated generally by reference numeral 20 and the preferred asphalt tracking system is designated generally by reference numeral 30. Exemplary mixing site 20 comprises a plurality of bins 32 adapted to receive, hold, and dispense components of asphalt mix such as aggregate material. Exemplary mixing site 20 also comprises conveyor 34 adapted to convey the asphalt mix from bins 32 to dryer 36.

Still referring to FIG. 1, preferred asphalt tracking system 30 is adapted to substantially continuously track an asphalt mix from a mixing site to a paving site and comprises a data collection system adapted to determine at least one characteristic of the asphalt mix. The preferred data collection system comprises a plurality of measuring devices such as weighbridge 40 and moisture sensor 42 that are adapted to determine a plurality of physical properties of the asphalt mix and communicate that data to data control system 44. The preferred data control system is adapted to receive data from the data collection system and comprises a controller that is adapted to communicate such data to a server. The preferred server is adapted to communicate such data to remote devices such as smartphones, tablets, laptop computers, desktop computers, and the like.

Still referring to FIG. 1, preferred asphalt tracking system 30 also comprises a lot tracking system. The preferred lot tracking system is adapted to track a lot or batch of the asphalt mix and comprises one or more dispensers 50 that are adapted to inject one or more tags 52 into the asphalt mix. It is contemplated within the scope of the invention that preferred dispensers 50 may inject preferred tags 52 at pre-determined regular intervals, but it is also contemplated within the scope of the invention that the dispensers may inject tags at irregular intervals or upon the determination of an out-of-specification asphalt mix and upon the return to in-specification asphalt mix. It is also contemplated within the scope of the invention that preferred dispensers 50 may be disposed on bins 32 or any other suitable location at mixing site 20.

Still referring to FIG. 1, preferred tags 52 comprises one or more RFID tags. The preferred RFID tags comprise an integrated circuit for storing and processing information, modulating and demodulating a radio frequency (RF) signal, collecting DC power from a reader signal, and other specialized functions. The preferred RFID tags also comprise an antenna for receiving and transmitting the signal. The preferred RFID tag information is stored in a non-volatile memory. The preferred RFID tag includes either fixed or programmable logic for processing the information.

Still referring to FIG. 1, preferred tags 52 are adapted to communicate with preferred readers 60. More particularly, preferred tags 52 are adapted to communicate a unique identification or serial number which will be correlated to the lot or batch or asphalt mix in which they have been placed. Preferably, tags 52 are of approximately the same size and weight as the aggregate material in which they are placed in order to minimize or eliminate any upstream or downstream movement of the tags relative to the asphalt mix as the tags and asphalt mix are conveyed through the mixing site.

Still referring to FIG. 1, the preferred lot tracking system also comprises one or more readers 60. Preferred readers 60 are adapted to communicate with tags 52 and data control system 44. More particularly, preferred readers 60 are adapted to receive the unique identification or serial number from tags 52. Preferred readers 60 include one or more RFID readers adapted to transmit an encoded radio signal to interrogate the preferred tags 52. The preferred RFID tag receives the message and then responds with its unique identification or serial number or other information such as a stock number, a lot or batch number, a production date, and the like. Because the preferred RFID tags have unique identification or serial numbers, the preferred RFID reader can discriminate among several tags that might be within the range of the reader and read them simultaneously. Preferably, readers 60 are placed at stationary locations at the mixing site, but it is contemplated within the scope of the invention that the readers may be mobile.

Figure 2:
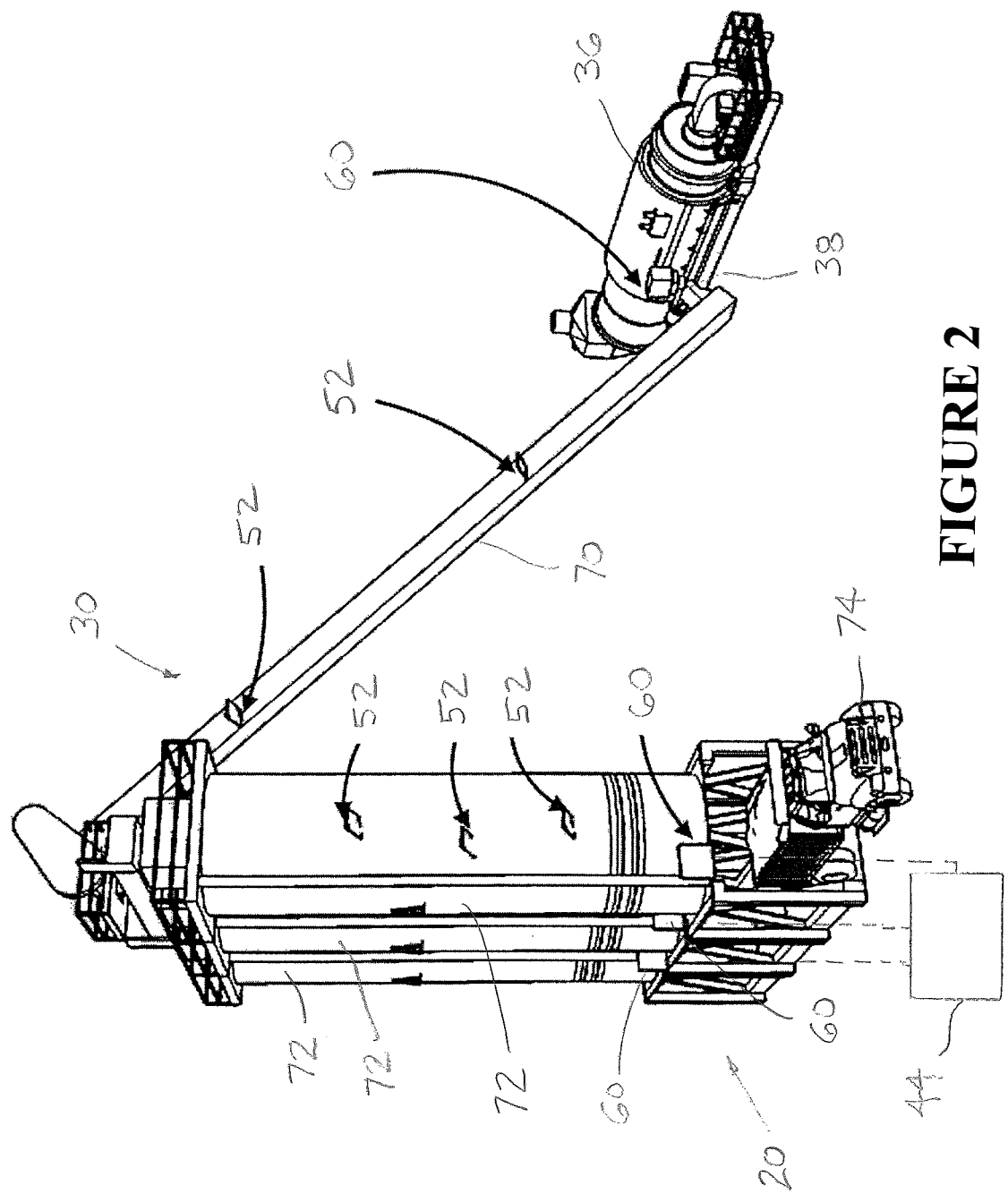
FIG. 2 is a perspective view of an exemplary mixing site utilizing the preferred asphalt tracking system illustrated in FIG. 1.

Referring now to FIG. 2, a perspective view of exemplary mixing site 20 utilizing preferred asphalt tracking system 30 is illustrated. As shown in FIG. 2, preferred tracking system 30 comprises dryer 36, mixer 38, a plurality of tags 52, a plurality of readers 60, conveyor 70 a plurality of silos 72, and truck 74.

Figure 3:
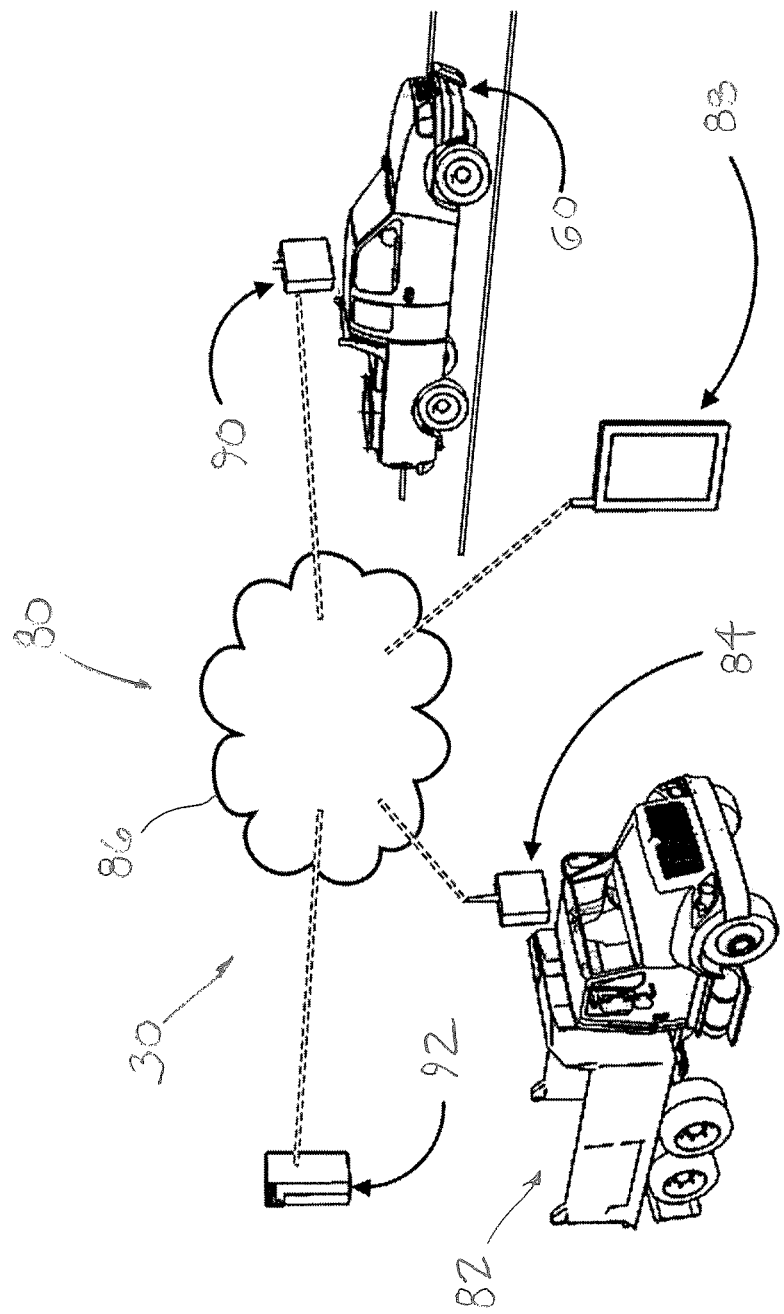
FIG. 3 is a perspective view of an exemplary communication network utilizing the preferred asphalt tracking system illustrated in FIGS. 1-2.

Referring now to FIG. 3, a perspective view of an exemplary communication network utilizing preferred asphalt tracking system 30 is illustrated. As shown in FIG. 3, the exemplary communication system is designated generally by reference numeral 80. Exemplary communication system includes preferred truck tracking system 82 which is adapted to track truck 74 as it travels from the mixing site to the paving site. Preferred truck tracking system 82 comprises GPS device 84 which is adapted to communicate with server 86. Preferred server 86 is also adapted to communicate with remote devices such as smartphone 88 and laptop computer 90 and produce paperless sales ticket 92.

Figure 4:
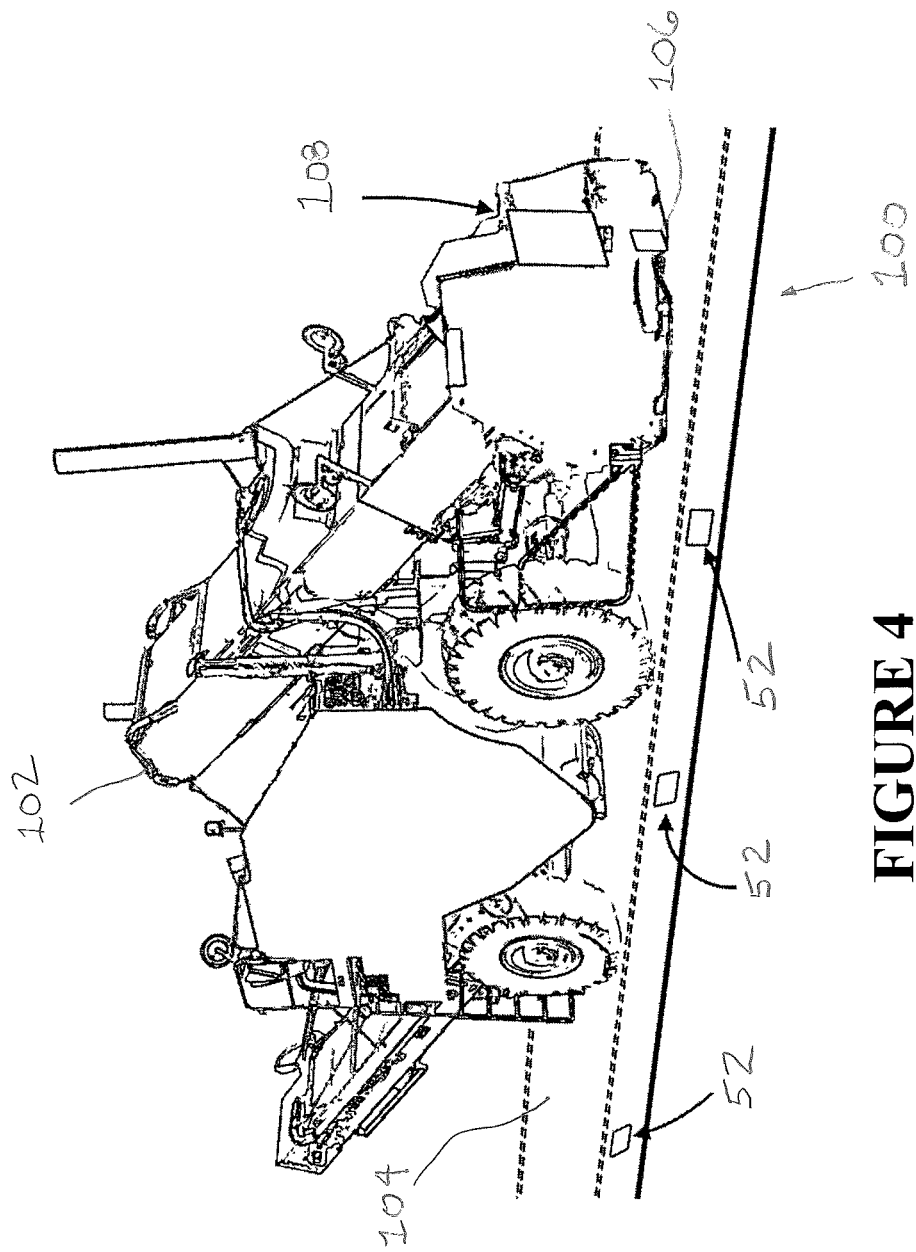
FIG. 4 is a perspective view an exemplary paving site utilizing the preferred asphalt tracking system illustrated in FIGS. 1-3.

Referring now to FIG. 4, a perspective view an exemplary paving site utilizing preferred asphalt tracking system 30 is illustrated. As shown in FIG. 4, the exemplary paving site is designated generally by reference numeral 100. Exemplary paving site 100 comprises material transfer vehicle 102, asphalt mat 104, and a pavement injection system. The preferred pavement injection system is adapted to identify the lot or batch of the asphalt mix and comprises a plurality of tags 52, paving site dispenser 106, and paving site reader 108. While FIG. 5 illustrates material transfer vehicle 102, it is contemplated within the scope of the invention that the pavement injection system may include a paver or a person for injecting tags into the asphalt mat.

Figure 5:
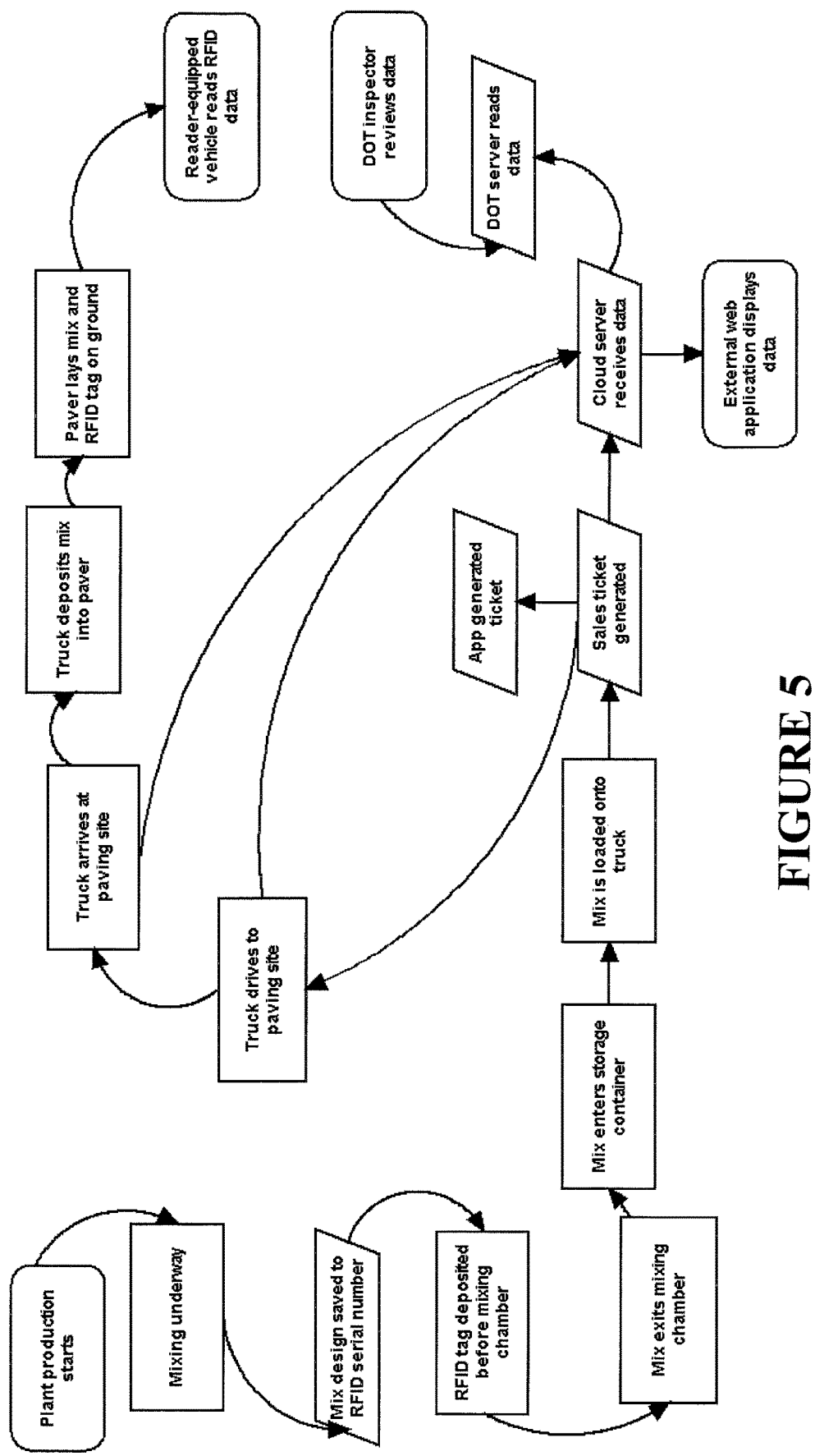
FIG. 5 is a flow chart illustrating the preferred method for tracking an asphalt mix in accordance with the present invention.

Referring now to FIG. 5, a flow chart of the preferred method for tracking an asphalt mix in accordance with the present invention is illustrated. As shown in FIG. 5, the preferred method for tracking an asphalt mix comprises providing an asphalt mix tracking system. The preferred asphalt mix tracking system comprises a data collection system that is adapted to determine at least one characteristic of the asphalt mix, a data control system that is adapted to receive data from the data collection system, a lot tracking system that is adapted to track a lot of the asphalt mix, a truck tracking system that is adapted to track a truck, and a pavement injection system that is adapted to identify the lot of the asphalt mix. The preferred asphalt mix tracking system is adapted to substantially continuously track the asphalt mix from a mixing site to a paving site. The preferred method for tracking an asphalt mix also comprises determining the at least one characteristic of the asphalt mix, communicating the at least one characteristic of the asphalt mix to the data control system, transporting the asphalt mix from the mixing site to the paving site, and injecting an identification means at the paving site.

In other preferred embodiments of the method for tracking an asphalt mix, the method further comprises communicating the at least one characteristic of the asphalt mix from the data control system to a server and communicating the at least one characteristic of the asphalt mix from the server to a remote device. In still other preferred embodiments of the method for tracking an asphalt mix, the method comprises injecting a tag into the asphalt mix at the mixing site and injecting a tag into the asphalt mix at the paving site. In other preferred embodiments of the method for tracking an asphalt mix, the method further comprises monitoring the temperature of the asphalt mix from the mixing site to the paving site, measuring the amount of time the asphalt mix is at the mixing site, measuring the amount of time the asphalt mix is in transit between a bin and a point of mixing, measuring the amount of time the asphalt mix is in transit between a point of mixing and a silo, and measuring the amount of time the asphalt mix is in transit between the mixing site and the paving site.

In operation, several advantages of the preferred embodiments of the system and method for asphalt mix tracking are achieved. For example, the preferred embodiments of the system and method for tracking an asphalt mix substantially continuously monitor the asphalt mix from the mixing site to the paving site. The preferred embodiments of the system and method for asphalt mix tracking identify and tag an out-of-specification lot or batch of asphalt mix, or any portion thereof. By so doing, the preferred embodiments of the system and method for asphalt mix tracking reduce waste and costs and provide only in-specification asphalt mix to paving sites. The preferred embodiments of the system and method for asphalt mix tracking also provide valuable data relating to the reclamation, recycling, durability, and lifespan of an asphalt mix. Further, the preferred embodiments of the system and method for asphalt mix tracking permit such valuable information to be collected long after the pavement is laid and via a vehicle equipped with a reader. In addition, the preferred embodiments of the system and method for asphalt mix tracking provides valuable data to multiple remote devices and users, including a Department of Transportation inspector, over a variety of platforms.

In addition, the preferred lot tracking system is adapted to tracks segment (lots) of material from the point of mix through the storage silos and into the truck. Lots are numbered and lot numbers on loadout tickets identify which lot the materials in each truck came from. Each lot record includes the lot number, time and date, a calibration security code (which changes upon any change to the mix, making it possible to identify unique calibrations), the name of the formula running, and any alarm conditions. The percentage and flow rate of each ingredient are also recorded, as well as lot size and/or duration and/or start/stop times. Average mix temperatures for the lot are recorded. This information may be printed and/or uploaded to a cloud server.

Further, the preferred truck tracking system uses GPS and RFID technologies to track the location of trucks and provide a detailed timing log. The log charts when the truck arrived at the plant, when it was loaded, the ticket number, material ID, truck ID, hauler ID, time of departure from the plant, time of arrival at the job site, and return trip details.

Still further, the preferred data control system is adapted to receive data from the preferred data collection system and upload the data to a cloud server. The truck driver may keep a physical copy of the data as a failsafe. A tablet in possession of a DOT official, a contractor, or an asphalt producer will be able to download the load data from the server. This streamlined process will eliminate the need to key in ticketing data for asphalt loads, improve customer satisfaction, and reduce labor requirements. Information will be written to RFID tags that will be injected into the mix itself. In this way, the tags will be embedded into the road at regular intervals.

Finally, the preferred pavement injection system uses the RFID tags injected into the road to provide a long-term record of the composition, age, and origin of the pavement. Vehicles equipped with an RFID reader will be able to travel the road and collect mix data. When the road has reached its lifespan, these sensors will provide reclamation data, such as asphalt cement percentage of the pavement, making the recycled material easier for contractors to re-use.

Although this description contains many specifics, these should not be construed as limiting the scope of the invention but as merely providing illustrations of some of the presently preferred embodiments thereof, as well as the best mode contemplated by the inventors of carrying out the invention. The invention, as described herein, is susceptible to various modifications and adaptations, and the same are intended to be comprehended within the meaning and range of equivalents of the appended claims.

What is claimed is:

1. A method of making data relating to asphalt mix available at a paving site where said asphalt mix has been used to form a section of pavement, the method comprising the steps of:
    (a) providing a tracking system that is configured to collect data related to the asphalt mix;
    (b) depositing one or more tags into the asphalt mix, each tag provided with a first set of data related to the asphalt mix into which it is deposited;
    (c) collecting and storing a second set of data related to the asphalt mix using the tracking system;
    (d) associating the first set of data with the corresponding second set of data in the tracking system;
    (e) depositing the asphalt mix at the paving site and forming the section of pavement;
    (f) after the section of pavement is formed, retrieving the first set of data from one of the tags in response to wireless interrogation by a reader;
    (g) wirelessly transmitting the first set of data sent from the one tag to the tracking system;
    (h) wirelessly receiving second set of data that is sent from the tracking system in response to the tracking system receiving the first set of data,
    wherein a first one or more tags are deposited into the asphalt mix at a mixing site at irregular intervals upon at least one of a determination of an out-of-specification asphalt mix and a determination that the asphalt mix has returned to within specification and a second one or more tags are deposited into the asphalt mix at the paving site.

2. The method of claim 1 wherein the second set of data is at least one of: the name of the formula of the asphalt mix; alarm conditions present or occurring during the mixing process of the asphalt mix; the name, weight, percentage flow rate of ingredients of the asphalt mix; lot size; start or stop times of mixing; duration of mixing; or an instantaneous or average temperature of asphalt mix.

3. The method of claim 1 wherein the second set of data is at least one of: total transit time for transporting the asphalt mix from the mixing site to the paving site; time the asphalt mix is located at the mixing site; transit time between a bin and the mixing site; or transit time between the mixing site and a silo.

4. The method of claim 1 further comprising providing a truck tracking system configured to track one or more vehicles conveying a lot of asphalt mix from a mixing site to the paving site, and providing at least one of location information and transit time information from the truck tracking system to the data control system, wherein the data control system is configured to associate the data received from the truck tracking system with the lot of asphalt mix transferred to the paving site.

5. The method of claim 1 wherein the second set of data is stored by the data control system to a server.

6. The method of claim 1, wherein the one or more tags are deposited into the asphalt mix at irregular intervals.

7. The method of claim 1, wherein the one or more tags are deposited into the asphalt mix at regular intervals.

8. The method of claim 1, wherein the first one or more tags identify a portion of asphalt mix that is out-of-specification, the method further comprising removing the out-of-specification portion of the asphalt mix prior to depositing the asphalt mix at the paving site and forming the section of pavement.

9. The method of claim 1 wherein the one or more tags are deposited into the asphalt mix at the paving site by a paving site dispenser after the asphalt material is deposited but before the asphalt mix hardens to pavement.

10. The method of claim 1 wherein the one or more tags are deposited into the asphalt mix at a mixing site.

11. The method of claim 1 further comprising wirelessly retrieving the stored data from the one or more tags using a reader carried by a vehicle traveling over the section of pavement.

12. The method of claim 1 wherein the data collected by the tracking system includes at least one non-location characteristic.

13. The method of claim 1 wherein the data is collected before the asphalt mix is deposited at the paving site.

14. The method of claim 1 wherein the second set of data received at step (h) is received by the reader.

15. The method of claim 1 wherein the second set of data received at step (h) is received by a wireless device that is not the reader.

16. A method of making data relating to asphalt mix available at a paving site where said asphalt mix has been used to form a section of pavement, the method comprising the steps of:
  (a) providing a tracking system that is configured to collect data related to the asphalt mix;
  (b) depositing one or more tags into the asphalt mix, each tag provided with a first set of data related to the asphalt mix into which it is deposited;
  (c) collecting and storing a second set of data related to the asphalt mix using the tracking system;
  (d) associating the first set of data with the corresponding second set of data in the tracking system;
  (e) depositing the asphalt mix at the paving site and forming the section of pavement;
  (f) after the section of pavement is formed, retrieving the first set of data from one of the tags in response to wireless interrogation by a reader;
  (g) wirelessly transmitting the first set of data sent from the one tag to the tracking system;
  (h) wirelessly receiving second set of data that is sent from the tracking system in response to the tracking system receiving the first set of data,
  wherein a first one or more tags that identify a portion of asphalt mix that is out-of-specification are deposited into the asphalt mix at a mixing site at irregular intervals and a second one or more tags are deposited into the asphalt mix at the paving site, the method further comprising removing the out-of-specification portion of the asphalt mix prior to depositing the asphalt mix at the paving site and forming the section of pavement.

* * * * *